United States Patent [19]
Fischer et al.

[11] Patent Number: 5,919,476
[45] Date of Patent: Jul. 6, 1999

[54] REINFORCED GEL SHEETING FOR SCAR TREATMENT

[75] Inventors: Reid M. Fischer, Minneapolis; Kevin M. Vonderharr, Coon Rapids; Stephen M. Trinter, Eden Prairie, all of Minn.

[73] Assignee: PMT Corporation, Chanhassen, Minn.

[21] Appl. No.: 08/939,623

[22] Filed: Sep. 29, 1997

[51] Int. Cl.$^6$ .............................. A61L 15/16; A61L 15/00; A61F 13/00; A61F 15/00
[52] U.S. Cl. ..................... 424/443; 424/445; 424/446; 424/447; 602/42; 602/44; 602/47; 602/48; 602/54; 604/304; 604/308
[58] Field of Search ..................................... 424/443, 445, 424/446, 447; 602/42, 44, 47, 48, 54; 604/304, 308

[56] References Cited

U.S. PATENT DOCUMENTS

| | | | |
|---|---|---|---|
| 3,972,328 | 8/1976 | Chen | 602/56 |
| 4,289,125 | 9/1981 | Hung | 602/42 |
| 4,369,284 | 1/1983 | Chen . | |
| 4,593,049 | 6/1986 | Bauman et al. . | |
| 4,618,213 | 10/1986 | Chen . | |
| 4,834,979 | 5/1989 | Gale | 424/448 |
| 4,838,253 | 6/1989 | Brassington et al. | 602/48 |
| 4,991,574 | 2/1991 | Pocknell | 602/48 |
| 5,145,933 | 9/1992 | Grisoni et al. . | |
| 5,254,346 | 10/1993 | Tucker et al. | 424/449 |
| 5,262,468 | 11/1993 | Chen . | |
| 5,474,783 | 12/1995 | Miranda et al. | 424/448 |
| 5,487,899 | 1/1996 | Davis | 424/443 |
| 5,505,958 | 4/1996 | Bello et al. | 424/449 |
| 5,552,162 | 9/1996 | Lee | 424/646 |

OTHER PUBLICATIONS

"Post Surgical Breast Form", Geligne Medical, Plastic and Reconstructive Surgery, vol. 99, No. 3, Mar. 1997.
"Medical Z Mammopatch™ Gel Self Adhesive", Plastic and Reconstructive Surgery, vol. 100, No. 3, Sep. 1997.

*Primary Examiner*—Leon B. Lankford, Jr.
*Assistant Examiner*—Christopher R. Tate
*Attorney, Agent, or Firm*—Anthony G. Eggink

[57] ABSTRACT

A bandage in the form of a reinforced silicone gel sheet for the treatment of scar tissue is disclosed. The bandage consists of a first layer of silicone adapted to adhere to the skin, a second layer of polyester mesh fabric with a plurality of holes therethrough, which contacts the first layer, and a third layer of silicone. The third layer acts as a sealant and an adhesive when applied to the mesh fabric by projecting through the holes in the mesh fabric to seal the second layer and to laminate the second layer between the first layer and the third layer. The sealant effect of the third layer provides a non-adherent surface which enables the bandage to be worn underneath clothing. A method of manufacture is also disclosed.

22 Claims, 2 Drawing Sheets

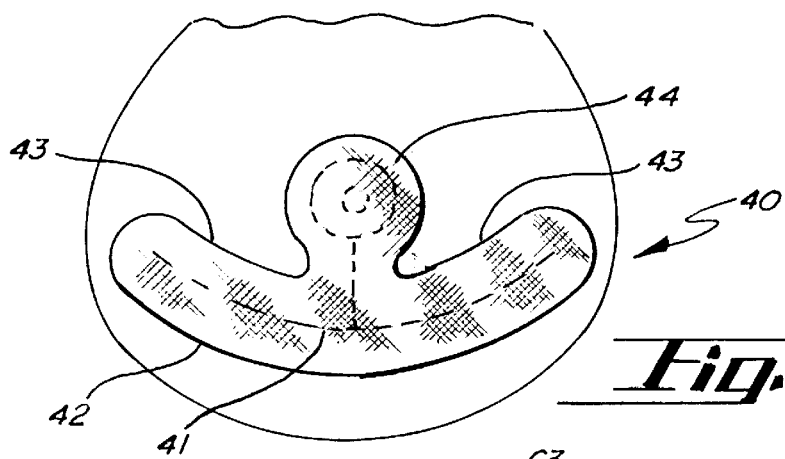
Fig. 5A.
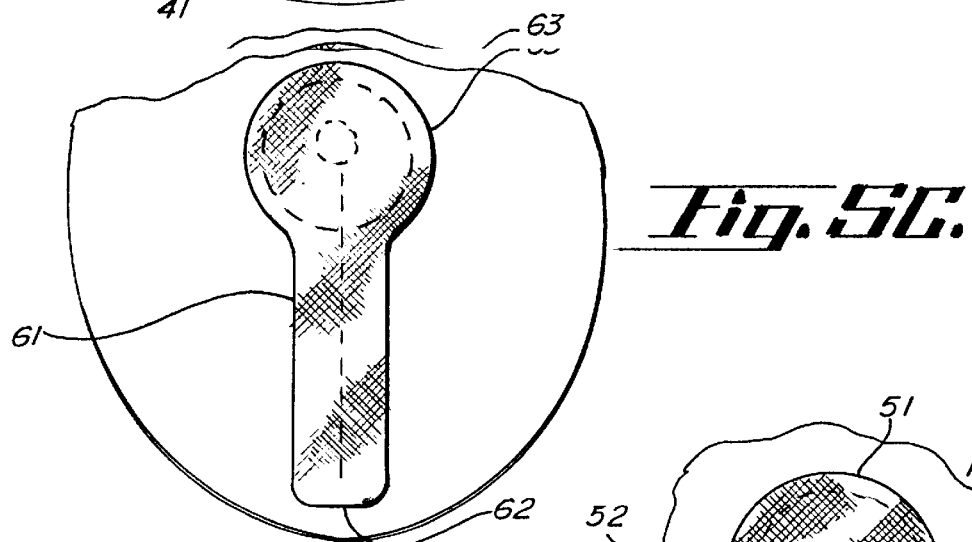
Fig. 5C.
Fig. 5B.
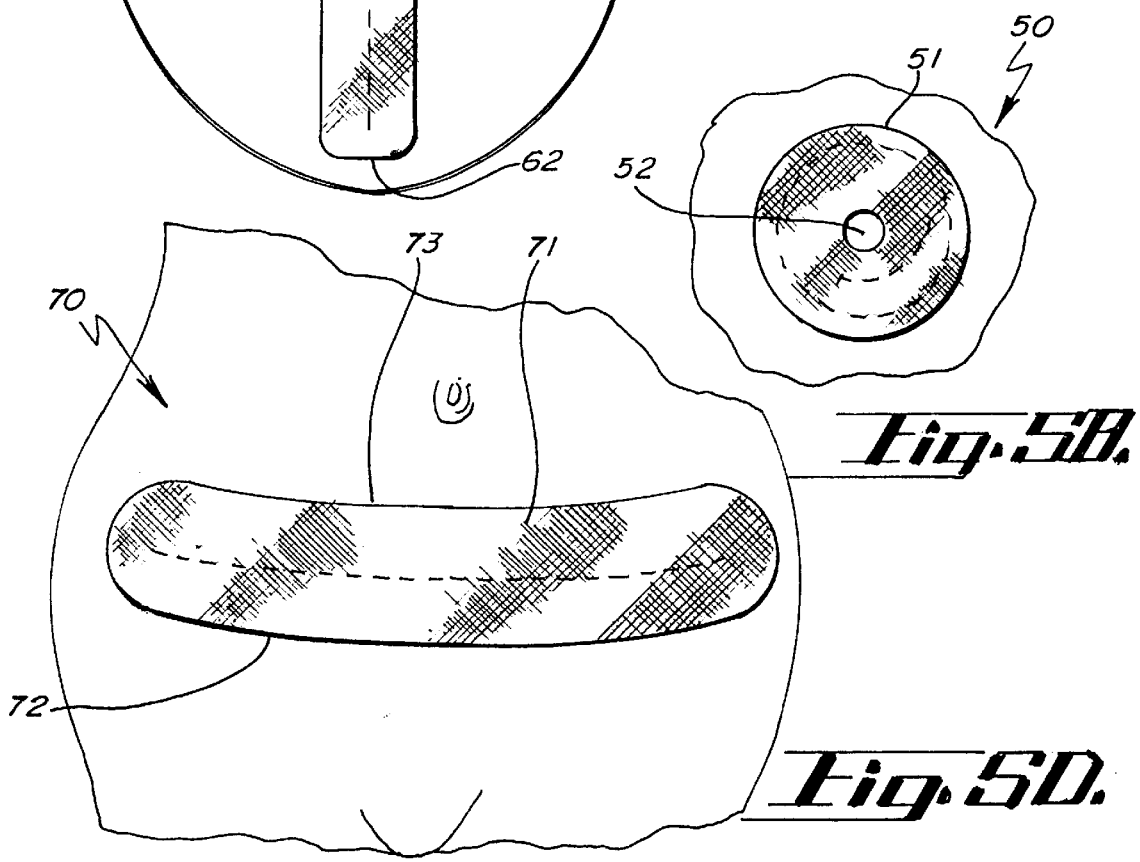
Fig. 5D.

5,919,476

REINFORCED GEL SHEETING FOR SCAR TREATMENT

BACKGROUND OF THE INVENTION

The present invention relates to a new and improved bandage for the treatment and rehabilitation of scar tissue wherein the bandage comprises a reinforced silicone gel sheeting.

When skin or dermis has been traumatized by cutting or burning, scar tissue is formed. In most cases, a small cut or burn area will result in a correspondingly small amount of scar tissue which is not readily discernable to a casual observer. In other cases, where the traumatized area is large and/or lengthy, scarring and scar tissue are quite apparent to a casual observer. This can not only be embarrassing for the person who is scarred, but can be a distraction for the casual observer. And, this can be particularly embarrassing to a person who has had elective surgery for cosmetic considerations. The problem is compounded when, over time, scar tissue tends to darken, become hypertrophic (thick) and project outwardly from the skin surface, thus becoming more apparent. Additionally, if the scar tissue happens to overlay a skeletal joint, movement of the joint is often painful and restricted. In the past, such complications were overcome by covering the scar tissue with clothing, make-up, or avoiding contact with other people. This strategy is often not possible nor desirable. Scar tissue and the tissue adjacent thereto can often become hyper-sensitive to contact with clothing, and often, a person will not cover scar tissue to the detriment of socialization. In some instances, a person might not be able to tolerate the application of make-up over scar tissue, again to the detriment of socialization. In other instances, a person may be required to wear a certain type or style of clothing which does not cover scar tissue locations.

Many medical care givers have recognized many of the problems associated with scar tissue and now include scar tissue management as part of the overall treatment of patients.

Silicone gels in the form of sheets have been used in the management of new scar tissue and hypertrophic keloid scarring resulting from elective surgery such as plastic surgery. It has been found that when the gels are positioned against scar tissue and pressure is applied thereto, the formation of hypertrophic scar tissue and attendant coloration can be reduced, resulting in a more normal appearance. Silicone gel sheets have the advantage over traditional bandages in that the gel adapts itself readily to the contours of the human body.

In the past, it has been found necessary to make silicone gels quite thick in order to prevent the gel from fragmenting during application and use. Although in the past, fiber nets have embedded in the silicone gel in an attempt to improve the strength and ease of handling of the silicone gel sheets, these attempts have not proved fruitful. See Pocknell, U.S. Pat. No. 4,991,574 at column 1, lines 66–68.

Additionally, gel sheets of the type that utilize silicone are tacky to the touch, both on the inner, body contacting surface and the exterior surface. Having a body contacting surface which is tacky to the touch is advantageous and desirable. Having an exterior which is tacky to the touch is not. A disadvantage of having a tacky exterior is that articles of clothing tend to adhere to the gel sheet. This presents several problems. One problem is that often the gel sheet adheres to an article of clothing with greater force than it adheres to the skin. Thus, when the article of clothing is removed, the gel sheet is removed from the body. Another problem is that articles of clothing will adhere to the gel sheet and prevent normal range of motion.

An additional problem encountered with gel sheets which are tacky to the touch is that they tend to become soiled more quickly.

The present invention solves the above problems by layering a polyester mesh fabric on top of a silicone gel sheet and then covering the mesh fabric with a layer of silicone which serves as a sealant and an adhesive for the mesh fabric by projecting through the holes in the fabric to bind the fabric to the silicone sheet. Thus, the mesh fabric is not embedded in the silicone sheet, but is layered on the sheet on the surface opposite that contacting the skin.

SUMMARY OF THE INVENTION

A bandage in the form of a reinforced silicone gel sheet for the treatment of scar tissue is disclosed. The bandage consists of a first layer of silicone adapted to adhere to the skin, a second layer of polyester mesh fabric with a plurality of holes therethrough, which contacts the first layer, and a third layer of silicone. The third layer acts as a sealant and an adhesive when applied to the mesh fabric by projecting through the holes in the mesh fabric to seal the second layer and to laminate the second layer between the first layer and the third layer. As will be explained below, the first layer has different properties than that of the third layer, with the first layer having surfaces which are tacky to the touch and the third layer having surfaces which are not tacky to the touch. The combination of the three layers results in a reinforced bandage that has a body contacting surface which is tacky to the touch, and an exterior surface which is non-adherent and textured. A method of manufacture is also disclosed.

An object and advantage of the present invention is to provide a bandage for treatment and rehabilitation of scar tissue and hypertrophic scar tissue.

An object and advantage of the present invention is to provide a bandage that is thin and lightweight.

Another object and advantage of the present invention is to provide a bandage which readily conforms to contours of the human body.

Another object and advantage of the present invention is to provide a bandage which is tear resistant.

Another object and advantage of the present invention is to provide a bandage which may be cut to desired shapes.

Another object and advantage of the present invention is to provide a bandage which delivers medicaments to a user of the device.

Still another object and advantage of the present invention is to provide a bandage which does not adhere to clothing.

Other objects and advantages will become apparent upon reading the specification and appended claims.

BRIEF DESCRIPTION OF THE DRAWINGS

FIG. 5A depicts a plan view of a preferred shape of the bandage;

FIG. 5B depicts a plan view of a preferred shape of the bandage;

FIG. 5C depicts a plan view of a preferred shape of the bandage; and

FIG. 5D depicts a plan view of a preferred shape of the bandage.

DETAILED DESCRIPTION OF THE PREFERRED EMBODIMENTS

The present invention may be embodied in other specific forms without departing from the spirit or essential attributes thereof, and it is therefore desired that the present embodiment be considered in all respects as illustrative and not restrictive, reference being made to the appended claims rather than to the foregoing description to indicate the scope of the invention.

Figure 1:
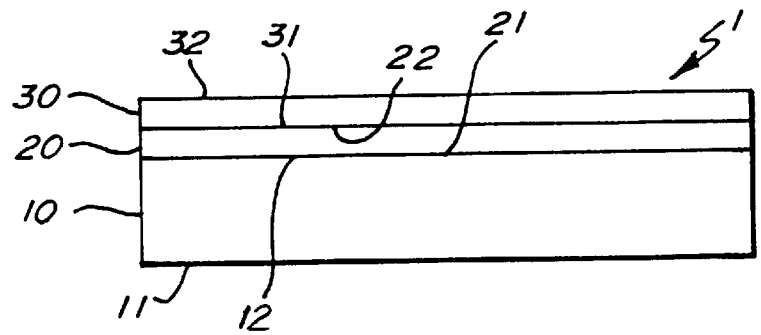
FIG. 1 depicts an edge view of the bandage showing the layered construction.

As seen in FIG. 1, the bandage of the present invention comprises three parts, a first layer 10, a second layer 20, and a third layer 30.

Preferably, the first layer 10 comprises a proximal or body contacting side 11 and a distal side 12. The first layer is preferably comprised of medical grade silicone which may or may not include medicaments such as Vitamin E, Vitamin C, Tretinoin (Retin-A), glycerin, lanolin, aloe, and cocoa butter.

The second layer 20 comprises a proximal side 21 and a distal side 22, with the proximal side 21 of the second layer in contact with the distal side 12 of the first layer 10. The second layer serves to reinforce the first layer and is preferably comprised of a mesh fabric, preferably polyester, which has been heat set to minimize shrinkage. However, it should be understood that the second layer may be fabricated from other fabrics, or sheet-like material with a plurality of interstices or holes.

The third layer 30 includes a proximal side 31 and a distal side 32 which define a thickness 33, with the proximal side 31 of the third layer in contact the distal side 22 of the second layer 20. The third layer 30 also includes a plurality of projections (not shown) which extend through interstices or holes (not shown) of the second layer 20 and come into contact with the distal side 12 of the first layer 10. The third layer serves three functions. The first is to seal the second layer, the second is to laminate the second layer to the first layer, and the third is to provide a non-adherent exterior surface. The third layer preferably comprises silicone. However, it is understood that other material may be used without departing from the scope of the invention.

Figure 2:
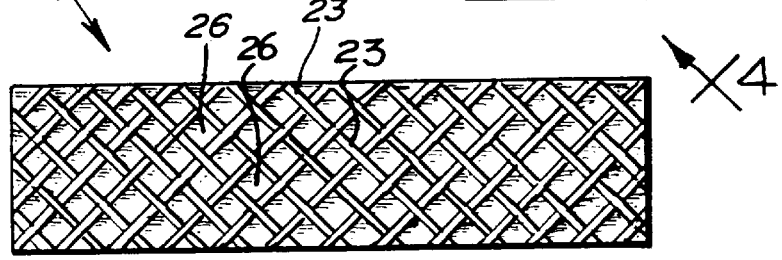
FIG. 2 depicts a top view of the bandage.

FIG. 2 shows a top view of the bandage of the present invention wherein the third layer overlies the second layer 20. It can be seen that the second layer comprises a plurality of fibers or strands 23 which form a mesh with a plurality of holes or interstices 26.

Figure 3:
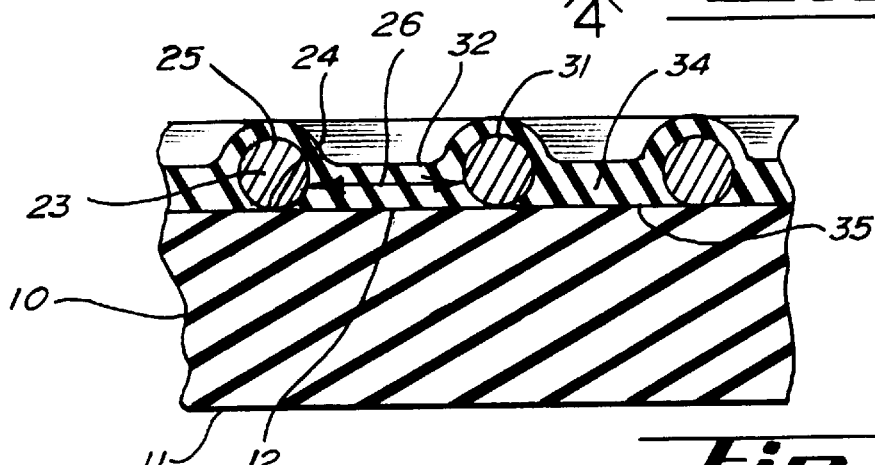
FIG. 3 depicts a detailed cross section of the layered bandage taken along lines A–A' of FIG. 2.

FIG. 3 shows a detailed cross-sectional view of FIG. 2 along line A–A'. In this figure, it can be seen that the proximal and distal sides 21, 22 of the second layer 20, as shown in FIG. 1, are comprised of a plurality of fibers or strands 23 which have proximal and distal sides 24, 25, respectively. When the second layer 20 is placed upon the distal side 12 of the first layer 10, it is the proximal sides 24 of the strands or fibers 23 which come into contact with the distal side of the first layer 10. And, when the third layer 30, is placed upon the distal side 22 of the second layer 20, it is the distal sides 25 of the strands or fibers 23 which come into contact with the proximal side 31 of the third layer 30. The third layer 30 has a plurality of projections 34 with proximal sides which extend through the interstices or holes 26 formed in the second layer 20 such that the proximal sides come into contact with the distal side 12 of the first layer 10.

As can be seen, the third layer 30 is thin enough to allow the contours of the second layer 20 to be maintained, so that the distal surface 32 of the third layer 30 has essentially the same texture as the second layer 20.

Figure 4:
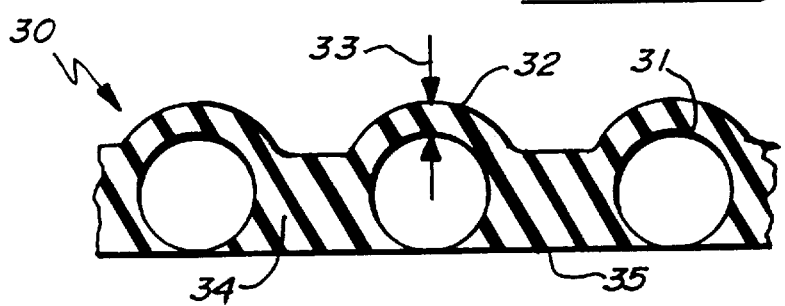
FIG. 4 depicts an edge view of a portion of the top layer of the bandage.

FIG. 4 shows another detailed view of the projections 34 which extend beyond the thickness 33 of the third layer 30. Here, the proximal side 35 of the projection 34 can be seen. Note that the projections 34 assume the shape of the interstices or holes as defined by the strands or fibers (not shown).

Although the bandage of the present invention may be used in cases of scar tissue resulting from unintentional or accidental trauma, it is particularly useful in the field of cosmetic surgery.

FIGS. 5A, 5B, 5C and 5D depict precut configurations of the bandage of the present invention for use in cosmetic surgical procedures.

FIG. 5A is a precut bandage configuration for use in reduction mammaplasties. The bandage 40 comprises an arcuate portion 41 having an outer circumference 42, an inner circumference 43, and a generally circular portion 44 which projects radially from the inner circumference 43 of the bandage 40.

FIG. 5B is a precut bandage configuration for use in mammaplasties. The bandage 50 comprises a generally circular portion 51 with an aperture 52 therein.

FIG. 5C is a precut bandage configuration. The bandage 60 comprises an elongated portion 61 having a first end 62 and a generally circular portion 63 attached opposite the first end 62 of the bandage 60.

FIG. 5D is a precut bandage configuration. The bandage 70 comprises an arcuate portion 71 having an outer circumference 72 and an inner circumference 73.

It should be understood that while FIGS. 5A–5D depict preferred embodiments of the bandage, the bandage may be configured to any desired or required shape without departing from the spirit and scope of the invention.

The bandage or reinforced gel sheeting of the present invention may be manufactured by the following steps: (1) pouring a silicone mixture into a mold, (2) curing the silicone mixture and the mold by the application of heat, (3) allowing the silicone mixture and the mold to cool, (4) placing a mesh fabric layer on the cooled silicone mixture, (5) spreading a sealant in a thin layer over the mesh fabric so that the sealant penetrates through holes in the mesh fabric and contacts the cooled silicone mixture, (6) curing the sealant, mesh fabric, and silicone mixture in the mold by the application of heat, (7) cooling the sealant, mesh fabric, and silicone mixture in the mold, and (8) removing the reinforced gel sheeting from the mold.

The silicone mixture used in the first layer preferably comprises three components, all of which may be commercially obtained. The first component, known as Part A (dimethyl methylvinyl siloxane) is the base (or resin). The second component, known as Part B (methyl vinyl dimethyl methylhydrogen siloxane, or dimethyl methylhydrogen siloxane) is a cross linker (or curing agent). The third component, known as Part C (polydivinyl siloxane) reduces the viscosity of the mixture and allows air bubbles to escape prior to setting.

The three components are blended together in the ratio of 15:1:22.5 of Part A to Part B to Part C by weight for at least three or four minutes to ensure complete mixing. Although this ratio is preferred, the ratios of the components may be varied as desired.

At this point, medicaments such as, but not limited to, Vitamin E, Vitamin C, Tretinoin (Retin-A), glycerin, lanolin, aloe, and cocoa butter may be added. If the use of medicaments is not desired, this step may be omitted.

The mixture is then poured into a suitably sized, planar mold to a preferred uniform thickness or depth of around 0.079" (2.000 mm). It is understood that the practitioner in the art may use planar molds of different configurations without departing from the spirit and scope of the invention.

The mold and the mixture are then allowed to sit for about thirty minutes to enable embedded air bubbles to escape. As an alternative, this step may be accelerated by subjecting the mold and mixture to negative pressure (i.e. a partial vacuum), if desired.

The mold and mixture are then baked at 221° F. (105° C.) for about sixty minutes to cure the mixture. The heated mold and mixture are then cooled to room temperature.

Next, a layer of polyester mesh or fabric (also commercially available) is positioned on the cured mixture surface as it sits in the mold. Although thin polyester fabric on the order of 0.009" (0.2286 mm) of thickness is utilized, the use of other materials which are thin and resist tearing is envisioned without departing from the spirit and scope of the invention. Such material could also be in the form of a solid sheet that has been provided with a plurality of apertures.

The third layer is then applied. Preferably, the third layer comprises RTV (room temperature vulcanization) Silicone dispersion in Xylene (also commercially available). The RTV Silicone is spread evenly over the second layer to a thickness of about 0.002" (0.0508 mm). Although RTV Silicone dispersion in Xylene is preferred, it is understood that other RTV materials may be utilized without departing from the spirit and scope of the invention.

The mold, mixture, fabric layer, and the silicone layer are then baked at 221° F. (105° C.) for about sixty minutes. As stated previously, the RTV Silicone dispersion serves three functions. The first function is to seal the fabric or second layer which overlies the mixture. The second function is to laminate the second layer between the mixture and the RTV Silicone dispersion, thus forming the bandage or reinforced gel sheeting. The third function is to provide a non-adherent exterior surface.

The mold, mixture, fabric layer, and the silicone layer are then cooled to room temperature. When the RTV dispersion has cured, it gives the fabric or second layer a non-tacky feel.

The step of heating the mold, mixture, and RTV dispersion may be omitted, if desired. However, heating is preferred because it tends to remove odors.

Next, the bandage or reinforced gel sheeting is removed from the mold and placed onto a relatively thick packaging substrate.

Although the bandage or reinforced gel sheeting may be applied to scar tissue as is, it may be necessary or desirable to form the bandage into other shapes. This may be accomplished by methods known in the cutting or shaping art.

What is claimed:

1. A bandage for the treatment of scar tissue, comprising:
   a) a tacky, skin contacting first layer comprising a generally non-textured, tacky silicone sheet having a predetermined shape and being adapted to adhere to the skin;
   b) a reinforcing second layer coextensive of said first layer and comprising a non-liquid permeable mesh fabric support structure having a plurality of holes therethrough, the second layer contacting the first layer; and
   c) a non-tacky, bonding third layer coextensive with said first and second layers overlaying and projecting through said holes in the second layer thereby occluding said holes and laminating the third layer to the first layer thereby securing said second layer between said first layer and said third layer.

2. The bandage of claim 1, wherein the first layer has a thickness of about 0.079 inch (2.000 mm).

3. The bandage of claim 2, wherein the second layer has a thickness of about 0.009 inch (0.2286 mm).

4. The bandage of claim 3, wherein the third layer has a thickness of about 0.002 inch (0.0508 mm).

5. The bandage of claim 1, having a thickness of less than about 0.15 inch (3.810 mm).

6. The bandage of claim 1, wherein the second layer comprises polyester that has been heat set to minimize shrinkage.

7. The bandage of claim 1, wherein a portion of the first layer further comprises a medicament.

8. The bandage of claim 1, adapted to conform to the human breast.

9. The bandage of claim 1, adapted to conform to the human abdomen.

10. The bandage of claim 1, adapted to conform to the area around the human mouth.

11. The bandage of claim 1, adapted to conform to the area around the human eyes.

12. The bandage of claim 1, wherein said third layer has an exterior which is textured.

13. A bandage for the treatment of scar tissue, comprising:
   a) a tacky, skin contacting first layer comprising a generally non-textured, tacky silicone, with the first layer adapted to adhere to the skin wherein the first layer includes a medicament;
   b) a reinforcing second layer comprising a mesh fabric structure having a plurality of holes therethrough, the second layer contacting the first layer; and
   c) a non-tacky, bonding third layer overlaying and projecting through said holes in the second layer, thereby occluding said holes and securing the second layer to the first layer by contacting said first.

14. The bandage of claim 13 wherein the medicament is Vitamin E.

15. The bandage of claim 13 wherein the medicament is Tretinoin.

16. The bandage of claim 13 wherein the medicament is aloe.

17. A bandage for the treatment of scar tissue, comprising:
   a) a tacky, skin-contacting first layer comprising a generally non-textured, tacky silicone adapted to adhere to the skin, wherein the first layer has a first predetermined thickness;
   b) a reinforcing second layer comprising a mesh fabric support structure having a plurality of holes therethrough, the second layer contacting the first layer and having a second predetermined thickness; and
   c) a non-tacky, bonding third layer overlaying and projecting through said holes in the second layer thereby occluding said holes and securing the second layer to the first layer by contacting said first layer, the third layer having a third predetermined thickness, wherein said first layer has a greater thickness than said second layer and wherein said second layer has a greater thickness than said third layer.

18. The bandage of claim 17, wherein the second layer comprises polyester.

19. The bandage of claim 17, wherein the third layer comprises silicone.

20. The bandage of claim 17, wherein the first layer includes a medicament.

21. The bandage of claim 17, wherein said first layer has a thickness of approximately 0.079 inches (2.000 mm), wherein said second layer has a thickness of approximately 0.009 inches (0.2286 mm) and wherein said third layer has a thickness of approximately 0.002 inches (0.0508 mm).

22. The bandage of claim 17, wherein a relatively thick packaging substrate is provided onto said first layer of said bandage.

* * * * *